ABSTRACT

United States Patent [19]
Glamkowski

[11] 3,947,447
[45] Mar. 30, 1976

[54] 5H-AMINOACETAMIDO-10,11-DIHYDRODIBENZ-[b,f]AZEPINES AND IMMEDIATE PRECURSORS

[75] Inventor: Edward J. Glamkowski, Warren, N.J.

[73] Assignee: American Hoechst Corporation, Bridgewater, N.J.

[22] Filed: May 20, 1974

[21] Appl. No.: 471,890

[52] U.S. Cl.. 260/268 TR; 260/239 D; 260/293.59; 424/244; 424/250; 425/267
[51] Int. Cl.$^2$............... C07D 223/18; C07D 295/06
[58] Field of Search............................. 260/268 TR

[56] References Cited
UNITED STATES PATENTS

| | | | |
|---|---|---|---|
| 2,981,736 | 4/1961 | Gailliot et al................. | 260/268 TR |
| 3,016,373 | 1/1962 | Saggionio et al............. | 260/268 TR |
| 3,125,576 | 3/1964 | Biel............................... | 260/268 TR |
| 3,133,068 | 5/1964 | Schindler...................... | 260/268 TR |

*Primary Examiner*—R. Gallagher
*Assistant Examiner*—D. B. Springer
*Attorney, Agent, or Firm*—Curtis, Morris & Safford

[57] ABSTRACT

5H-Aminoacetamido-10,11-dihydrodibenz[b,f]azepines and their physiologically tolerable acid addition salts are disclosed to be useful as central nervous system depressant agents with anticonvulsant and muscle relaxing activity and as antihypertensive agents. A process for their preparation and for the preparation of their novel precursors is also described.

7 Claims, No Drawings

5H-AMINOACETAMIDO-10,11-DIHYDRODIBENZ-[B,F]AZEPINES AND IMMEDIATE PRECURSORS

This invention relates to 5H-aminoacetamido-10,11-dihydrodibenz[b,f]azepines and their utility as central nervous system depressant agents with anticonvulsant and muscle relaxing activity and as antihypertension agents; their immediate precursors and a process for the preparation thereof.

To the best of our knowledge, the compounds of this invention have not heretofore been described. Hydrazide derivatives of 5-amino-10,11-dihydrodibenz[b,f]azepines are reported [R. W. Woodward et al., J. Med. Chem., 14, 1131 (1971)] as having antimalarial and antimicrobial activity.

The compounds of the invention conform to the formulae:

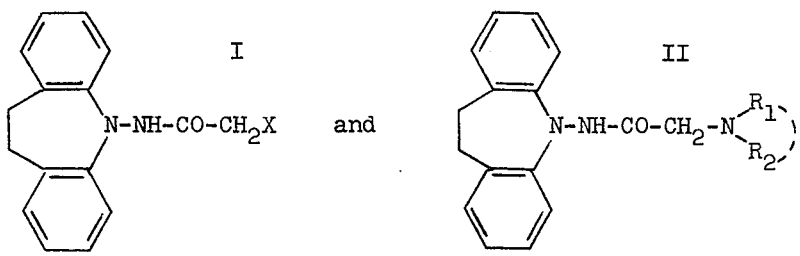

wherein X represents halogen, $R_1$ is hydrogen or alkyl of from 1 to 3 carbon atoms, $R_2$ is alkyl of from 1 to 3 carbon atoms or phenyl, and $R_1$ and $R_2$ together with the nitrogen atom to which they are attached are piperidinyl, piperazinyl or piperazinyl substituted in the 4-position by alkyl of from 1 to 4 carbon atoms, hydroxyalkyl of from 1 to 4 carbon atoms, alkoxyalkyl of from 2 to 5 carbon atoms, phenylalkyl of from 7 to 9 carbon atoms, acyloxyalkyl of from 3 to 5 carbon atoms, phenyl, chlorophenyl, methoxyphenyl or trifluoromethylphenyl. The physiologically tolerable acid addition salts thereof are included within the scope of the invention. The compounds of Formula II are preferred.

In accordance with the process of the invention, the compounds are prepared by acylating 5H-amino-10,11-dihydrodibenz[b,f]azepine (reported in British Pat. No. 1,035,449 and Chemical Abstracts, Vol. 65, 12180) with a halogen acetylhalide in the presence or absence of a suitable organic solvent, such as benzene, tetrahydrofuran and the like, to yield the precursor compounds of the invention as shown in the equation:

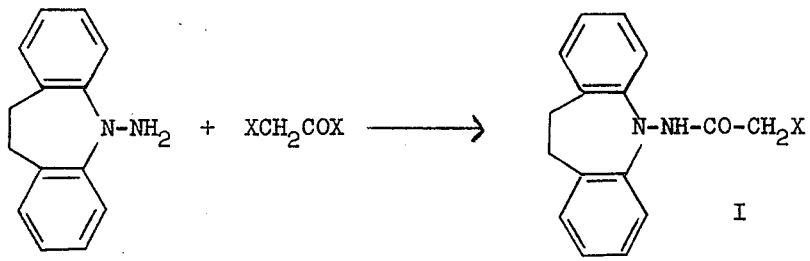

The precursor compounds of Formula I are reacted with a suitable amine in the presence or absence of a solvent for several minutes to 24 hours at a temperature of from 0° to 120°C. to prepare the compounds of Formula II. In a preferred embodiment, the reaction is carried out in boiling methanol as the reaction medium.

When $R_1$ and $R_2$ together with the nitrogen to which they are attached are a 4-(hydroxyalkyl)-piperazinyl group, the hydroxy group can be acylated with a suitable aliphatic acid or derivative thereof in an organic solvent to convert it into the corresponding acyloxyalkyl piperazine group. In a preferred method, the aliphatic acid derivative is an anhydride and the organic solvent is benzene.

The anticonvulsant activity of the compounds of the invention was tested by the methods of J. W. Bastian et al. [J.W. Bastian, W.E. Krause, S.A. Ridlon, and N. Ercoli, J. Pharmacol. Exptl. Therap., 127, 75 (1959)], and Swinyard et al. [H.A. Swinyard, W.C. Brown, and L.S. Goodman, ibid., 106, 319 (1952)]. Male COBS mice were challenged with electroshock and strychnine and the intraperitoneal dose protecting 50% of the mice ($PD_{50}$) against the extensor tonic phase induced by electroshock and strychnine injection are shown in Table I for some of the compounds of the invention.

Table I

| Compound | Electroshock $PD_{50}$, mg/kg. | strychnine $PD_{50}$, mg/kg. |
|---|---|---|
| 5H-(4-methyl-1-piperazinyl)-acetamido-10,11-dihydrodibenz-[b,f]azepine | 37 | 54 |
| 5H-(4-n-propyl-1-piperazinyl)-acetamido-10,11-dihydrodibenz-[b,f]azepine | 88 | 75 |
| 5H-(4-β-hydroxyethyl-1-piperazinyl)acetamido-10,11-dihydrodibenz[b,f]azepine | — | 25 |

The compounds of the invention are also useful as tranquilizers because of their depressant effects on the central nervous system. The depressant effects on the central nervous system were evaluated according to the mouse observation procedure of S. Irwin, Psychopharmacologia, 13, 222 (1968). Male COBS mice are dosed with the drug, and its effects on behavior and reflex depression together with muscle relaxation are determined by the degree of deviation from control scores, with activity expressed in terms of minimum effective dose (MED) in milligrams per kilogram of body weight. For example, 5H-(4-β-acetoxyethyl-1-piperazinyl)-acetamido-10,11-dihydrodibenz[b,f]azepine shows a MED of 40.

The muscle relaxation ability of the compounds of the invention was illustrated according to the procedure of N.W. Dunham and T.S. Miya, J. Amer. Pharm. Assoc., 46, 208, (1957). Male COBS mice that had exhibited an ability to remain on a wooden rod, 1.5 inches in diameter, rotating at 8.7 r.p.m. for 1 minute were dosed with the drug, and its muscle relaxation effects determined by the degree of deviation from control scores, with activity expressed in terms of that dose ($ED_{50}$ in mg/kg.) causing 50% of the group of mice to fall off the rod. For example, 5H-(4-β-hydroxyethyl-1-piperazinyl)acetamido-10,11-dihydrodibenz[b,f]-azepine shows an $ED_{50}$ of 24.

The compounds of the invention are also useful as antihypertensive agents. This activity of the compounds is demonstrated by their ability to lower blood pressure when tested in the spontaneous hypertensive rat by the indirect tail cuff method described in "Methods of Pharmacology," Vol. 1, edited by A. Schwartz, Appleton-Century-Crofts, New York, N.Y., p. 135 (1971). For example, at a dose of 100 mg/kg. of body weight, 5H-(4-n-propyl-1-piperazinyl)-acetamido-10,11-dihydrodibenz[b,f]azepine exhibits a 35 mm of Hg drop in blood pressure on the 3rd day.

The compounds of the invention may be administered to a patient by any convenient route such as orally, intramuscularly, intravenously, subcutaneously, or intraperitoneally. The preferred route of administration is oral, for example, with an inert diluent, with an edible carrier, in gelatin capsules, or tablets.

For the purpose of oral therapeutic administration, the active compounds of this invention may be incorporated with excipients and used in the form of tablets, troches, capsules, elixirs, suspensions, syrups, and the like. These preparations should contain at least 0.5% of the active compound, but may be varied depending upon the particular form and may conveniently be between 7% to about 70% by weight of the unit. The amount of active compound in such compositions is such that a suitable dosage will be obtained. Preferred compositions and preparations according to the present invention are prepared so that an oral dosage unit form contains between 0.5 and 200 milligrams of active compound.

The tablets, pills, capsules, troches, and the like may also contain the following ingredients: a binder such as gum tragacanth or gelatin; an excipient such as starch or lactose, a disintegrating agent such as alginic acid, potato starch and the like; a lubricant such as magnesium stearate; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or both. A syrup may contain, in addition to the active compounds sucrose as a sweetening agent, and certain preservatives, dyes and colorings, and flavors. Materials used in preparing these various compositions must be pharmaceutically pure and nontoxic in the amounts utilized.

Acids useful for preparing the pharmaceutically acceptable acid addition salts of the invention include inorganic acids such as hydrochloric, hydrobromic, sulfuric, nitric, phosphoric and perchloric acids, as well as organic acids such as oxalic, tartaric, citric, acetic, succinic, maleic and ethane disulfonic acids.

EXAMPLE 1

11.4 ml. of chloracetyl chloride in 50 ml. of benzene are added to a well stirred solution of 21.0 g of 5H-amino-10,11-dihydrodibenz[b,f]azepine in 300 ml. of benzene. The resulting mixture is refluxed for one hour, during which time a gelatinous precipitate changes to feathery crystals. This mixture is cooled to 20° with exclusion of moisture, filtered, washed with benzene, then with ether and dried. The crystalline material is recrystallized from ethanol to give pure white silken needles, m.p. 221°–222°, of 5H-chloroacetamido-10,11-dihydrodibenz[b,f] azepine.

Analysis: Calc. for $C_{16}H_{15}ClN_2O$: 67.02% C; 5.27% H; 9.77% N Found :66.75% C; 5.21% H; 9.69% N.

EXAMPLE 2

24.2 g. of bromoacetyl bromide are added to a stirred solution of 18.9 g of 5H-amino-10,11-dihydrodibenz[b,f]azepine in 350 ml. of methylene chloride with exclusion of moisture. After 1.5 hours, the thick mixture is dissolved in 1.5 l. of methylene chloride and the solution is extracted with 250 ml of 10% sodium hydroxide, then with dilute aqueous sodium chloride solution. The organic layer is dried over sodium sulfate and concentrated to a crystalline solid. This is recrystallized from anhydrous ethyl alcohol to give 5H-bromoacetamido-10,11-dihydrodibenz [b,f]azepine, m.p. 207°–209°C.

Analysis: Calc. for $C_{16}H_{15}BrN_2O$ : 58.02% C; 4.56% H; 8.46% N. Found: 57.95% C; 4.60% H; 8.39% N.

EXAMPLE 3

A stirred mixture of 4.30 g of 5H-chloroacetamido-10,11-dihydrodibenz[b,f]azepine (Example 1) in 43 ml. of methanol is immersed in a 100°C. oil bath. 5 ml. of piperidine are added to the boiling mixture. After 5 minutes a solution results and after another 5 minutes the product begins to separate. After a total of 15 minutes in the hot bath, 30 ml. of water are added dropwise over a 5 minute period. The mixture is removed from the hot bath and stirred until it reaches ambient temperature. The mixture is filtered, the filter cake is washed with water and dried to yield a white solid. This is recrystallized from an isopropanol benzene mixture to give silken needles, m.p. 207.5°–209°C., of 5H-(1-piperidinyl)acetamido-10,11-dihydrodibenz[b,f]azepine.

Analysis: Calc. for $C_{21}H_{25}N_3O$ : 75.19% C; 7.51% H; 12.53% N. Found: 75.18% C; 7.59% H; 12.57% N.

EXAMPLE 4

A stirred slurry of 4.30 g of 5H-chloroacetamido-10,11-dihydrodibenz[b,f]azepine (Example 1) in 43 ml. of methanol is immersed in a 100°C. oil bath. 10 ml. of a 40% aqueous solution of dimethylamine are added to the boiling mixture. The mixture is allowed to boil for 30 minutes, and then water is added dropwise over a 5 minute period. The mixture is removed from the hot bath and stirred until it reaches ambient temperature. The mixture is filtered, the cake washed with water and dried to give an off-white product. The product is recrystallized from isopropanol and then from a benzene hexane mixture to give white flakes, m.p. 188°–190°C., of 5H-dimethylaminoacetamido-10,11-dihydrodibenz[b,f]azepine.

Analysis: Calc. for $C_{18}H_{21}N_3O$ : 73.19% C; 7.17% H; 14.23% N. Found: 73.12% C; 7.20% H; 14.22% N.

Following the same general procedure with dipropylamine instead of dimethylamine results in the preparation of 5H-dipropylaminoacetamido-10,11-dihydrodibenz[b,f]azepine.

EXAMPLE 5

A stirred slurry of 4.30 g of 5H-chloroacetamido-10,11-dihydrodibenz[b,f]azepine (Example 1) in 43 ml. of methanol is treated with 5 ml. of N-methylpiperazine by the manipulative procedure described above in Example 4 to give white flates, m.p. 202°–204°C., of 5H-(4-methyl-1-piperazinyl)-acetamido-10,11-dihydrodibenz[b,f]azepine.

Analysis: Calc. for $C_{21}H_{26}N_4O$ : 71.97% C; 7.48% H; 15.99% N. Found: 72.11% C; 7.65% H; 15.90% N.

EXAMPLE 6

A stirred slurry of 7.17 g of 5H-chloroacetamido-10,11-dihydrodibenz[b,f]azepine (Example 1) in 50 ml. of methanol is immersed in a 100°C. oil bath, and a solution of 9.77 g of N-β-hydroxyethylpiperazine in 25 ml. of methanol is added in one portion. After 45 minutes, 75 ml. of water are added in portions to precipitate the product. The mixture is removed from the heating bath and stirred until the mixture reaches ambient temperature. The mixture is filtered, the cake is washed with water and dried to give off-white crystals. The crystals are recrystallized twice from ethanol and once from acetone to give white flakes, m.p. 194°–196°C., of 5H-(4-β-hydroxyethyl-1-piperazinyl)-acetamido-10,11-dihydrodibenz[b,f]azepine.

Analysis: Calc. for $C_{22}H_{28}N_4O_2$ : 69.45% C; 7.42% H; 14.72% N. Found: 69.34% C; 7.39% H; 14.78% N.

By reacting with N-γ-hydroxypropylpiperazine and N-β-propoxyethylpiperazine instead of N-β-hydroxyethylpiperazine, 5H-(4-γ-hydroxypropyl-1-piperazinyl)acetamido-10,11-dihydrodibenz[b,f]azepine and 5H-(4-β-propoxyethyl 1-piperazinyl)-acetamido-10,11-dihydrodibenz[b,f]azepine, respectively are formed.

EXAMPLE 7

A stirred mixture of 7.17 g of 5H-chloroacetamido-10,11-dihydrodibenz[b,f]azepine in 100 ml. of tetrahydrofuran is warmed briefly on a steam bath to effect solution. To this is added, in one portion, 10 ml. of a 40% aqueous solution of methylamine and the solution is stirred at ambient temperature for one hour, then at reflux for one hour. 500 ml. of water are added to the hot solution to precipitate the product. The mixture is filtered, the cake is washed with water and dried to give an almost white solid. The solid is recrystallized three times from a benzene cyclohexane mixture to give white micro-crystals, m.p. 160°–162°C., of 5H-methylaminoacetamido-10,11-dihydrodibenz[b,f]azepine.

Analysis: Calc. for $C_{17}H_{19}N_3O$ : 72.57% C; 6.81% H; 14.93% N. Found: 72.63% C; 6.93% H; 15.02% N.

By reacting with aniline instead of methylamine, 5H-phenylaminoacetamido-10,11-dihydrodibenz[b,f]azepine is formed.

EXAMPLE 8 a. A sample of 17.4 g of 4-n-propylpiperazine.2HBr is partitioned between 150 ml. of methylene chloride and 100 ml of 3N-sodium hydroxide. The organic layer is separated and 100 ml. of saturated sodium chloride solution are added to the aqueous layer. The aqueous phase is extracted further with (2×50 ml.) of methylene chloride, and the combined organic phases are back-extracted with 100 ml. of saturated sodium chloride solution. The organic layer is dried and concentrated to a crystalline solid of 4-n-propylpiperazine.

b. A stirred slurry of 8.60 g of 5H-chloroacetamido-10,11-dihydrodibenz[b,f]azepine (Example 1) in 50 ml. of tetrahydrofuran is warmed briefly to effect solution. To this is added a solution of the 4-n-propylpiperazine, as obtained in Part a), in 50 ml. of tetrahydrofuran. The solution is refluxed for one hour, and then 250 ml. of water are added portionwise to precipitate a gummy semi-solid. The mixture is cooled and filtered. The cake is triturated on the funnel with water to give a fine white solid which is filtered and dried. The solid is recrystallized twice from absolute ethanol to give white crystals, m.p. 197°–200°C., of 5H-(4-n-propyl-1-piperazinyl)acetamido-10,11-dihydrodibenz[b,f]azepine.

Analysis: Calc. for $C_{23}H_{30}N_4O$ : 72.98% C; 7.99% H; 14.80% N. Found: 73.08% C; 7.92% H; 15.02% N.

EXAMPLE 9

5 ml. of acetic anhydride are added to a stirred slurry of 3.81 g of 5H-(4-β-hydroxyethyl-1-piperazinyl)acetamido-10,11-dihydrodibenz[b,f]azepine (Example 6) in 25 ml. of refluxing benzene. The mixture is refluxed for 30 minutes and 100 ml. of hexane are added to the hot solution. The product crystallizes and the mixture is cooled to 10°C., filtered, and the cake is washed with hexane and dried to give a tan crystalline solid. The solid is recrystallized twice from absolute ethanol to give the white ester, m.p. 164°–165°C., 5H-(4-β-acetoxyethyl-1-piperazinyl)acetamido-10,11-dihydrodibenz[b,f]azepine.

Analysis: Calc. for $C_{24}H_{30}N_4O$ : 68.22% C; 7.16% H; 13.26% N. Found: 68.44% C; 7.21% H; 13.44% N.

EXAMPLE 10

A solution of 7.30 g of N-phenylpiperazine in 25 ml. of ethanol is added to a stirred mixture of 4.97 g of 5H-bromoacetamido-10,11-dihydrodibenz[b,f]azepine (Example 2) in 125 ml. of ethanol immersed in a 100°C. oil bath. After a few minutes, a solution results followed shortly by heavy precipitation of the product. After 1 hour at 100°C., 100 ml. of water are added in portions to complete the precipitation, and the mixture is stirred at ambient temperature for 30 minutes. The mixture is filtered, the cake washed with water, and dried to give a white solid. The solid is recrystallized twice from dimethylformamide to give white crystals, m.p. 236°–238°C., of 5H-(4-phenyl-1-piperazinyl)-acetamido-10,11-dihydrodibenz[b,f]azepine.

Analysis: Calc. for $C_{26}H_{28}N_4O$ : 75.70% C; 6.84% H; 13.58% N. Found: 75.47% C; 6.87% H; 13.61% N.

EXAMPLE 11

A solution of 10.4 g of 4-α,α,α-trifluoro-m-tolylpiperazine in 25 ml. of tetrahydrofuran is added to a stirred solution of 4.97 g of 5H-bromoacetamido-10,11-dihydrodibenz[b,f]azepine (Example 2) in 75 ml. of tetrahydrofuran. Within a few minutes the product begins to crystallize voluminously and the stirred mixture is then immersed in a 100°C. oil bath for 30 minutes to complete the reaction. Water is added and the stirred mixture is allowed to cool to ambient temperature. The mixture is filtered, the cake washed well with water and dried to give a solid. The solid is recrystallized twice from dimethylformamide to give white crystals, m.p. 264°266°C., of 5H-(4-α,α,α-trifluoro-m-tolyl-1-piperazinyl)acetamido-10,11-dihydrodibenz[b,f]azepine.

Analysis: Calc. for $C_{27}H_{27}F_3N_4O$ : 67.49% C; 5.66% H; 11.66% N. Found: 67.22% C; 5.64% H; 11.47% N.

EXAMPLE 12

A stirred solution of 4.97 g of 5H-bromoacetamido-10,11-dihydrodibenz[b,f]azepine (Example 2) in 100 ml. of tetrahydrofuran is reacted with N-benzylpiperazine in 25 ml. of tetrahydrofuran by the manipulative procedure described above in Example 11 to give white crystals. The crystals are recrystallized twice from a chloroform and ether mixture to give crystals, m.p. 199°–201°C., of 5H-(4-benzyl-1-piperazinyl-)acetamido-10,11-dihydrodibenz[b,f]azepine.

Analysis: Calc. for $C_{27}H_{30}N_4O$ : 76.03% C; 7.09% H; 13.13% N. Found: 75.83% C; 7.08% H; 13.16% N.

EXAMPLE 13 a. The free base, 4(p-chlorophenyl)piperazine, is obtained from 10.8 g of 4-(p-chlorophenyl)-piperazine.2HCl by the manipulative procedure described in Example 8 (a).

b. A solution of the 4-(p-chlorophenyl)piperazine, as liberated in Part (a), in 150 ml. of tetrahydrofuran is added to a stirred solution of 6.62 g of 5H-bromoacetamido-10,11-dihydrodibenz[b,f]azepine (Example 2) in 100 ml. of tetrahydrofuran. A mild exothermic reaction ensues and then the product begins to separate voluminously from the initial solution within a few minutes. The mixture is stirred at ambient temperature for 15 minutes, and then at reflux for 30 minutes. Then 300 ml. of water are added portionwise and the mixture is filtered. The cake is washed with water, and dried. The product is recrystallized twice from dimethylformamide to give white crystals, m.p. 259°–261°C., of 5H-[4-(p-chlorophenyl)-1-piperazinyl]acetamido-10,11-dihydrodibenz-[b,f]azepine.

Analysis: Calc. for $C_{26}H_{27}ClN_4O$ : 69.87% C; 6.09% H; 12.53% N. Found: 69.94% C; 6.24% H; 12.70% N.

EXAMPLE 14 a. The free base 4-(p-methoxyphenyl)piperazine is liberated from 10.6 g of 4-(p-methoxyphenyl)-piperazine.2HCl by the manipulative procedure described above in Example 8 (a).

b. A warm stirred solution of 6.62 g of 5H-bromoacetamido-10,11-dihydrodibenz[b,f]azepine in 100 ml. of tetrahydrofuran is treated with the 4-(p-methoxyphenyl)-piperzine liberated in Part (a) by the manipulative procedure described in Example 13 (b) to give white crystals, m.p. 220°–224°C., dec., of 5H-[4-(p-methoxyphenyl)-1- piperazinyl]-acetamido-10,11-dihydrodibenz[b,f]azepine, m.p. 220°–224°C.

Analysis: Calc. for $C_{27}H_{30}N_4O_2$ : 73.28% C; 6.83% H; 12.66% N. Found : 73.36% C; 6.90% H; 12.84% N.

I claim:

1. A compound of the formula

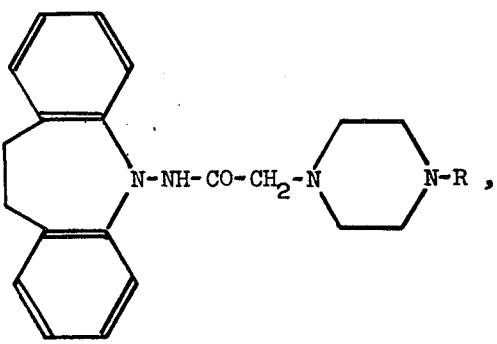

wherein R is hydrogen, alkyl having 1 to 4 carbon atoms, hydroxyalkyl having 1 to 4 carbon atoms, alkoxyalkyl having 2 to 5 carbon atoms, phenylalkyl having 7 to 9 carbon atoms, acetoxyalkyl having 3 to 5 carbon atoms, phenyl, chlorophenyl, methoxyphenyl, or trifluoromethylphenyl; and the physiologically tolerable acid addition salts thereof.

2. The compound defined in claim 1 which is 5H-(4-methyl-1-piperazinyl)acetamido-10,11-dihydrodibenz[b,f]-azepine; and the physiologically tolerable acid addition salts thereof.

3. The compound defined in claim 1, which is 5H-(4-β-hydroxyethyl-1-piperazinyl)acetamido-10,11-dihydrodibenz-[b,f]azepine; and the physiologically tolerable acid addition salts thereof.

4. The compound defined in claim 1, which is 5H-(4-benzyl-1-piperazinyl)acetamido-10,11-dihydrodibenz[b,f]-azepine; and the physiologically tolerable acid addition salts thereof.

5. The compound defined in claim 1, which is 5H-(4-β-acetoxyethyl-1-piperazinyl)acetamido-10,11-dihydrodibenz[b,f]azepine; and the physiologically tolerable acid addition salts thereof.

6. The compound defined in claim 1, which is 5H-(4-n-propyl-1-piperazinyl)acetamido-10,11-dihydrodibenz[b,f]-azepine; and the physiologically tolerable acid addition salts thereof.

7. A compound as in claim 1 wherein R is alkyl having 1 to 3 carbon atoms, hydroxyethyl, hydroxypropyl, propoxyethyl, benzyl, acetoxyethyl, phenyl, p-methoxyphenyl, p-chlorophenyl, or m-trifluoromethylphenyl; and the physiologically tolerable acid addition salts thereof.

* * * * *